(12) United States Patent
Charm et al.

(10) Patent No.: US 8,663,975 B2
(45) Date of Patent: Mar. 4, 2014

(54) METHOD AND APPARATUS FOR REDUCING LUMINESCENT TEST RESULT INTEREFERENCES (CONTINUATION)

(75) Inventors: Stanley E. Charm, Boston, MA (US); David R. Legg, Amesbury, MA (US); Richard T. Skiffington, North Reading, MA (US); Robert J. Markovsky, Brentwood, NH (US)

(73) Assignee: Charm Sciences, Inc., Lawrence, MA (US)

( * ) Notice: Subject to any disclaimer, the term of this patent is extended or adjusted under 35 U.S.C. 154(b) by 0 days.

(21) Appl. No.: 13/477,608

(22) Filed: May 22, 2012

(65) Prior Publication Data

US 2012/0231483 A1    Sep. 13, 2012

Related U.S. Application Data

(63) Continuation of application No. 12/442,774, filed on Mar. 25, 2009, now abandoned, which is a continuation of application No. PCT/US2007/001229, filed on Jan. 16, 2007.

(60) Provisional application No. 60/851,540, filed on Oct. 13, 2006.

(51) Int. Cl.
    *C12M 1/34*    (2006.01)

(52) U.S. Cl.
    USPC ......................................................... 435/287.1

(58) Field of Classification Search
    USPC ......................................................... 435/287.1
    See application file for complete search history.

(56) References Cited

U.S. PATENT DOCUMENTS

| 5,670,356 A | 9/1997 | Sherf et al. .................... 435/189 |
| 6,180,395 B1 | 1/2001 | Skiffington et al. ........ 435/287.6 |
| 6,891,058 B2 | 5/2005 | Zhao et al. .................... 558/401 |

OTHER PUBLICATIONS

Ptitsyn et al. "A Biosensor for Environmental Genotoxin Screening Based on an SOS lux Assay in Recombinant *Escherichia coli* Cells," Applied and Environmental Microbiology, vol. 63, No. 11, Nov. 1997, pp. 4377-4384.

Bowie, "Synthesis of Firefly Luciferin and Structural Analogs," In Methods in Enzymology, 1978, Edited by M. DeLuca, vol. 57, pp. 15-28, Especially Fig. 5A, pp. 22-23 in ISR, copy not available.

*Primary Examiner* — Bin Shen
(74) *Attorney, Agent, or Firm* — MacCord Mason PLLC

(57) ABSTRACT

This application involves detecting luminescence. Various methods and devices are described that reduce interference of ambient light, including UV radiation, on test results. Such methods and devices include using UV blocking material and covering test components prior to use.

19 Claims, 1 Drawing Sheet

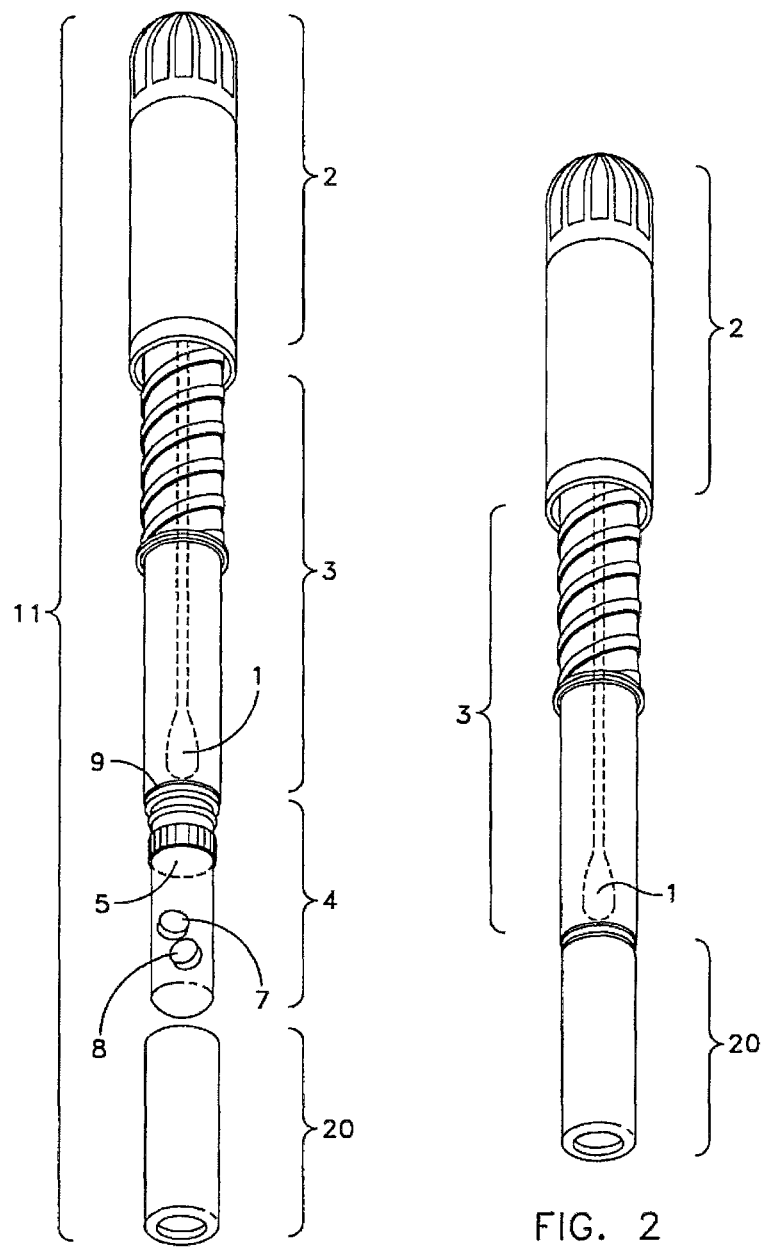

METHOD AND APPARATUS FOR REDUCING LUMINESCENT TEST RESULT INTEREFERENCES (CONTINUATION)

RELATED APPLICATIONS

This application is a continuation of application Ser. No. 12/442,774 filed Mar. 25, 2009, which is a continuation of PCT/US07/01229 filed Jan. 16, 2007, which claims the benefit of U.S. Provisional Application Ser. No. 60/851,540 filed Oct. 13, 2006.

FIELD OF THE TECHNOLOGY

The present disclosure relates generally to hygiene monitoring, and more particularly to reducing test result interference in hygiene monitoring in food processing, food service and health care.

BACKGROUND

Measuring cleanliness in industrial, food processing, food service, health care and other settings is important for maintaining good hygiene and sanitation. For example, the surfaces of equipment used for food handling, storage or processing can be a major source of microbial and allergen contamination. Microbial contamination can lead to decreased shelf life of products and, if pathogenic, transmission of disease. Allergen contamination can cause adverse reactions in sensitive people including hives, anaphylaxis and death.

Microbial culturing can determine the presence of microorganisms. Culturing is, however, time consuming and, as a result, the necessary "real time" feedback to sanitation and food preparation personnel may not be available. It is, therefore, possible that food exposed to surfaces that are later found to contain potentially harmful microorganisms could enter the food supply.

Rapid and efficient test methods and devices are available for the detection of contamination on surfaces. Some of these methods do not detect microbes directly but instead use markers such as adenosine triphosphate (ATP) that are indicative of the presence of microbes or residual food contamination of a surface. For example, those described in U.S. Pat. No. 6,055,050 (Photometer and Test Sample Holder for use therein, Method and System) issued Apr. 25, 2000; and U.S. Pat. No. 6,180,395 (Reagent Chamber for Test Apparatus and Test Apparatus), issued Nov. 30, 2001, both of which are incorporated herein by reference. A commercially available apparatus that detects ATP is the POCKETSWAB-PLUS (POCKETSWAB is a registered trademark of Charm Sciences, Inc. of Lawrence, Mass.), which rapidly and efficiently detects ATP on surfaces. The POCKETSWAB detects ATP by emission of luminescence (light) from the reaction of luciferin and luciferase in the presence of ATP. The luminescence can be measured using a luminometer.

Specific allergen tests are typically in the ELISA (enzyme linked immunosorbent assay) format and require 30 minutes or more to obtain a result. Historically, ELISA allergen tests were more sensitive than ATP tests for detecting allergenic food residues. Recently, however, highly sensitive ATP detection assays and systems, particularly single service ATP detection assays, have been used to rapidly screen a surface for food residue at a level of allergen test detection that is consistent with sensitivity of available ELISA methods. Such a test is described in U.S. Pat. No. 7,132,249, issued Nov. 7, 2006 (Method of Determining Allergenic Food on Surfaces), incorporated herein by reference. For tests that detect certain allergens, such as peanut allergens, regulations require sensitivity at particular levels, such as 5 parts per million peanut allergen. The ALLERGIENE (ALLERGIENE is a registered trademark of Charm Sciences, Inc., Lawrence, Mass.) ATP test detects ATP with sensitivity adequate to be used as an indicator for potential allergen contamination.

With increased sensitivity to ATP the problem of interference from background noise may increase. Minimizing or eliminating this problem can help avoid false results and provide better signal to noise ratios in not only highly sensitive ATP systems but also less sensitive ATP systems. Similarly, luminescence based tests, other than those relying on the luciferin/luciferase ATP reaction, may also benefit from methods and devices for reducing background noise.

Therefore, Applicants desire a system and method for hygiene monitoring without the drawbacks presented by the traditional systems and methods.

SUMMARY

In accordance with the present disclosure, an apparatus and method is provided for reducing luminescent test result interferences. This disclosure provides an improved apparatus that is convenient, efficient, and safe for the user, particularly when used during hygiene monitoring. This disclosure may allow for methods of reducing interferences during luminescent testing and analysis.

In one aspect, a test sample is obtained and combined with reagents that generate luminescence, such as luciferin and luciferase. The combining can occur either within a test vial or prior to adding the sample and reagents to the test vial. The test vial may be characterized in that it allows luminescence generated within the test vial to be detected outside the test vial, for example, a transparent test vial. The test vial can include a material that reduces the amount of ultraviolet ("UV") radiation that can penetrate the test vial, such as a UV blocking/filtering material ("UV block") that can be mixed into the test vial raw material. A buffer can also be included to optimize reaction conditions. The luminescence output is detected using an instrument such as a photomultiplier or photodiode based instrument. The test vial raw material can include a combination of plastic materials, including, for example, polypropylene and polyethylene. The UV block can be, for example, CIBA Shelf life Plus UV1100. Typical combinations include about 99.5% plastic to about 0.5% UV block. An additional method for blocking interfering UV radiation includes covering the test vial. The cover can be designed to be capable of removal prior to detecting luminescence. A retractable covering may also be useful. The methods and apparatuses can be used monitor the hygiene of a surface such as an inanimate food contact surface.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which:

FIG. 1 is an exploded view of a removable light blocking sleeve separated from the test device according to an embodiment of the disclosure; and FIG. 2 is a perspective view of the embodiment of FIG. 1 where the removable sleeve is positioned in a light blocking position on the test device.

DESCRIPTION OF EMBODIMENTS

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawings in general and FIG. 1 in particular, it will be understood that the illustrations are for the purpose of describing embodiments of the disclosure and are not intended to limit the disclosure or any invention thereto. As best seen in FIG. 1, an apparatus is shown embodied according to the present disclosure. FIG. 1 shows the format of a swab type device 11. The swab 1 is removed by gripping the swab handle 2, and a surface, such as a food contact surface, is swabbed using the swab 1. The swab 1 can be provided pre-moistened. Alternatively the swab 1 can be dipped into the sample or the sample can be pipetted onto the swab 1. The swab 1 is then reinserted into the body 3 and screwed longitudinally through the covering 9 of the test vial 4 and through the seal 5 and into bottom of the test vial 4. The liquid within the sealed compartment (between covering 9 and seal 5) at the top of the test vial 4 flows into contact with the test reagent 7 and dissolves the reagent 7 containing luciferin-luciferase. An optional desiccant 8 can also be included at the bottom of the test vial 4. Alternatively, the luciferin and luciferase reagents can be in the sealed compartment at the top of the test vial with the solution in the bottom of the test vial 4. The test vial 4 can be composed of a material that at least partially blocks light including UV radiation. Also shown is the removable test vial cover 20. The test vial cover 20 preferably remains in place until insertion into a luminometer for reading, at which time the removable test vial cover 20 is removed from the test vial 4. UV block material can be incorporated into the plastic test vial 4 material. Luminescence is detected by inserting the test vial 4 into a luminometer.

FIG. 2 shows the test vial cover 20 in position covering the test vial 4.

Containers used for reagents and samples from which luminescence is detected can be transparent to allow the luminescence generated therein to be detected, for example by a photodiode, photomultiplier tube or other device capable of measuring such output. However, such containers may allow UV radiation to penetrate in to the reagents and/or sample. Similarly, UV radiation may be absorbed by other materials used such as swabs or the plastic used to make the container. If that absorbed light is not allowed to dissipate, an increase in the results provided by detectors, such as photomultiplier tubes and photodiodes, can result.

In an embodiment, a material to reduce UV transmittal is added to the plastic used to make the test containers. Such UV block has been found to reduce the effect of UV radiation exposure on test results while not reducing detection of luminescence generated by the sample and reagents within the container.

To prevent UV absorption by test components including test containers some embodiments include a removable sleeve-like covering. The cover may also be retractable. Also it may be possible to simply instruct the user to cup the vial in his/her hand to prevent excessive light exposure.

Covering test components minimizes or eliminates external energy absorption (for example UV radiation), and the related luminescence caused by such absorption, that may cause increased background counts. Covering test components also increases choice of both the test components and the materials used to produce the test components. The covering can be composed of a variety of material such as paper, plastic, metal. In one embodiment, the covering was composed of a layer of Kraft paper liner surrounded by a black glaze outer layer. One end can be closed for example with a curl and disc closure and the covering can be dimensioned for a friction fit against all or a portion of the exterior wall of the test vial.

Reagents can include luciferin and luciferase or other light generating reagents. Buffers are often also provided to optimize the environment. The reagents can also include a variety of substances to aid in releasing ATP from cells. Such substances can be combined in buffers or provided separately.

Test components and test component materials that can be useful to enhance sample detection include materials and/or components that are excitable by the emission wavelength of the biochemical reaction of ATP with luciferin and luciferase. By including such material, the ATP reaction may be better detected. However, such materials and/or components may also be excitable by external light sources, thereby increasing test background (noise) unless adequately covered. For example, test components, such as white or light colored swab tips, light or white colored swab shafts and energy absorbing plastics, may enhance sample detection by enhancing the luminescence generated in the ATP reaction. These same materials, however, when left uncovered, may be susceptible to excitation by ambient light thereby increasing test background. By providing adequate covering the impact of such ambient light can be limited while benefiting from the additional light excitation.

In an embodiment contact of UV radiation with test materials is reduced by including a UV block material within the test vial. Although UV block may not completely block all UV radiation from contacting the test components; UV block can substantially reduce the amount of UV radiation contacting the test components. For example, plastic test vials, such as test vials formed from olefin based fibers such as polypropylene and polyethylene, can include UV block material incorporated into the vial plastic material. One typical container is a test vial. Vials can be molded such as by injection molding, blow molding or extrusion molding.

Test vials can be composed of a variety of materials such as plastics. Plastics with low energy absorbance properties, such as olefin based plastics, may be useful. For example, a molded test vial can include material such as Ciba SHELFPLUS UV 1100. In one example, 0.5% Ciba SHELFPLUS UV 1100 was combined with 99.5% Marlex RLC-350 (clarified polypropylene random copolymer, antistatic, controlled rheology). Other UV filter material may be usefully employed such as the variety available from CIBA. Generally, UV block material and/or light blocking covers may be useful to limit interference with any of the variety of test apparatus and methods in which luminescent signals provide results. These filtering and/or blocking techniques may be particularly useful when operating at the limits of sensitivity and selectivity.

A variety of luminescence detectors (luminometers), including photomultiplier tube and/or photodiode based detectors, can be used to read the luminescent output. The luminometer may be used in combination with a system including reagents for generation of luminescence in the presence of ATP. The luminescence reader may, for example, be in the format of the LUMINATOR-K, LUMINATOR-T, FIREFLY, LUM-96, LUMGIENE and NOVALUM readers (LUMINATOR-K, LUMINATOR-T, FIREFLY, LUM-96, LUMGIENE AND NOVALUM are trademarks of Charm Sciences, Inc.; Lawrence, Mass.) The luminescence reader may also be in the format of any luminescence reading device such as a photodiode, or a photomultiplier based luminometer. In some embodiments the luminometer can include an optical lens filter, such as a UV filter, covering the lens of the luminometer. Optical filters can be used alone or with the other techniques for blocking light described herein. Such optical filters can be composed of, for example, glass or plastic.

In some embodiments, the luminescence reader can be programmed to delay the beginning of the reading for a period of time to allow luminescence, from test components absorption of external energy, such as UV radiation, to dissipate. Delayed reading can be used alone or with the other methods and devices described herein for limiting energy, particularly UV radiation, absorption by test components.

In some embodiments the system includes using a colored swab and/or shaft, such as a dark colored swab, for example a blue swab with a black shaft. Such dark colored or black swab and swab shaft can be used to reduce the amount of energy such as light that is absorbed and/or reflected by the system that does not relate to ATP luminescence from the sample. Some embodiments can include autoclavable components such autoclavable swabs to allow elimination of residual ATP from the test materials. In some embodiments a blue foam or black foam swab tip made of polyurethane and black swab shafts composed of polypropylene, were used. In other embodiments the shaft was composed of polycarbonate. Other possibly useful colored plastics include polyester. Swabs can be attached to the shaft without adhesives that could be a source of ATP or excitable from external energy sources.

In addition to the various luciferin, luciferase, buffers, detergents and other reagents described herein, it is possible to use the methods and devices for counting and extrapolating described herein with other reagent systems, particularly those for measuring and detecting ATP. In various embodiments, reagents allowing regeneration of ATP, such as described by Foote et al, U.S. Pat. No. 6,043,047, issued Mar. 28, 2000 and regeneration of luciferin such as described by Kurosawa et al, EP 1 306 435 A1, published May 2, 2003, may be used.

When other reagents within the test vial are dry, such as in tablet or powder form, a desiccant can also be provided within the test vial. One useful desiccant is molecular sieve 4.times.8 mesh desiccant (AGM Container Controls, Inc. Tucson, Ariz.). Desiccants can also include color indicators that change color in the presence of moisture. A desiccant can be chosen that does not absorb significant UV radiation and/or does not emit luminescence that would interfere with the luminescence generated by the test reagents and the sample.

The following examples demonstrate the efficacy and utility of the present inventions.

EXAMPLES

Example 1

Concentrations of luciferin and luciferase of 0.0233 micrograms luciferase per microliter buffer and 0.233 micrograms luciferin per microliter buffer were used. With increased concentrations the importance of reducing background noises, increases. The following results compare luminescence results at time 0 through time 600 seconds of exposure of a white swab to light followed by detection of luminescence generated from other than sample ATP (no sample was obtained). Detection was using a NOVALUM (NOVALUM is a trademark of Charm Sciences, Inc. Lawrence, Mass.) test instrument. Data showed consistently increasing luminescence results as follows:

| TIME (SECONDS) | RELATIVE LIGHT UNITS |
|---|---|
| 0 | 71557 |
| 10 | 80296 |
| 20 | 91866 |
| 30 | 133949 |
| 40 | 138238 |
| 50 | 120353 |
| 60 | 114479 |
| 120 | 147771 |
| 180 | 239893 |
| 240 | 262627 |
| 300 | 223965 |
| 360 | 236004 |
| 420 | 288903 |
| 480 | 375826 |
| 540 | 230596 |
| 600 | 200906 |

In experiments conducted using the procedure of cupping the bottom, transparent test vial portion with a hand and exposing the swab tip to external light only for as long as necessary to obtain a sample (approximately 5-20 seconds), an average result of 77211 (average of 10 results) was obtained thereby demonstrating the importance of shielding test components from ambient light Example 2

Data in the following table 1 was generated using ALLERGIENE Swabs and a NOVALUM luminometer which included UV block in the vial material. Results are in relative light units (RLU). n=20 tests at each condition. The UV block composition used for this example was 0.5% CIBA Shelflife Plus UV1100 (CIBA is a registered trademark of Ciba Specialty Chemical Corporation, Tarrytown, N.Y.) combined with 99.5% MARLEX RLC-350 (clarified polypropylene random copolymer, antistatic, controlled rheology) (MARLEX is a registered trademark of Phillips Petroleum Company, Tex.). Column heading "Low UV ATP Negative" includes results from exposing test vials, with negative ATP control, to normal laboratory light low UV (4-5 uW/cm2). Column heading "Low UV, ATP Positive" includes results in standard laboratory light with a positive control of 0.02 femtomoles (finoles) ATP. Column heading "High UV ATP Negative" includes results using negative ATP control and exposing the test vials to window filtered natural cloud filtered sunlight, high UV (68-111 uW/cm2).

The results show that the presence of ATP reduces the effect of photoluminescence from higher levels of ambient light. At elevated UV light (high UV), the RLU count for the ATP Negative tests increased 8-16 times without the CIBA Shelflife Plus UV block and 3-5 times with the CIBA Shelflife Plus UV block. The SD was lower with the UV block included. Based on these results, with the typically variable UV exposure encountered in the field, the % CV compared to negative results will likely also decrease when UV block is used.

The Low UV ATP Negative results have no background subtract (the background subtract can be programmed into the luminometer) so that the negatives values can be analyzed; with the background subtract the results would be 0. The High UV ATP Negative results have the 107,000 background subtract deducted to show actual relative light unit ("RLU") results that a typical user in the filed would obtain. The higher CV with the LOW UV ATP Negative is most likely due to a random RLU spike in one of the sample. Such a spike is seen in approximately 1 of 30 results. Removing the results reflected by this random spike in one result, the average is 82,600 and the CV is 10% (in parenthesis).

TABLE 1

|  |  | Low UV ATP Negative | Low UV ATP Positive (0.02 fmoles) | High UV ATP Negative |
|---|---|---|---|---|
| No UV Block | Average | 86,000 | 165,000 | 897,000 |
|  | SD | 6,200 | 23,000 | 163,000 |
|  | CV | 7% | 14% | 18% |
| UV Block | Average | 87,000 (82,600) | 171,000 | 256,000 |
|  | SD | 14,900 (8,000) | 25,000 | 43,000 |
|  | CV | 17% (10%) | 15% | 17% |

Example 3

Combining the low and high UV exposure data demonstrates the improvement provided by including UV block in the vial plastic. Tables 2A (without background subtract) and 2B (with 107,000 background subtract) show reductions in both average results and standard deviation (SD) when CIBA UV 1100 is included in the vial plastic. Note that the higher CVs are the result of the data being from 3 different levels of UV light. However, the reduction in average and SD are clearly shown.

TABLE 2A

|  | Control (without UV filter) | With CIBA UV 1100 |
|---|---|---|
| Average | 391,312 | 191,098 |
| SD | 432,064 | 128,520 |
| CV | 110% | 67% |

TABLE 2B

|  | Control (without UV filter) | With CIBA UV 1100 |
|---|---|---|
| Average | 291,662 | 91,061 |
| SD | 426,948 | 120,379 |
| CV | 146% | 134% |

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular fauns "a," "an," and "the" include plural referents unless expressly and unequivocally limited to one referent.

What is claimed is:

1. A method for detecting luminescence comprising:
   a) obtaining a test sample;
   b) combining the test sample with reagents that generate luminescence to create a mixture,
      wherein the combining occurs either within a test vial or prior to adding the mixture to the test vial, the test vial comprising a combination of a plastic material and a light stabilizing UV blocking material;
   c) detecting the luminescence generated within the test vial.

2. The method of claim 1 wherein the plastic material is combined with the UV blocking material at a ratio of about 99.5% plastic to about 0.5% UV block.

3. The method of claim 1 wherein the plastic material comprises polypropylene.

4. The method of claim 1 wherein the UV blocking material comprises CIBA Shelflife Plus.

5. The method of claim 1 wherein the luminescence is generated by the combination of luciferin, luciferase and ATP.

6. The method of claim 1 wherein the detection of luminescence is used to monitor the hygiene of a surface.

7. The method of claim 1 further comprising covering the test vial with a removable cover, the removable cover being capable of blocking light from contacting the test vial.

8. The method of claim 7 wherein the covering is retractable.

9. The method of claim I wherein the test vial is transparent.

10. The method of claim 1 wherein the UV blocking material prevents a portion of UV radiation from contacting the mixture of sample and reagents.

11. The method of claim 1 wherein the UV blocking material prevents substantially all external UV radiation from contacting the mixture of sample and reagents.

12. The method of claim 1 wherein said detecting comprises inserting the test vial into a luminometer and wherein said luminometer is configured to delay detection of luminescence for a period of time, said period of time chosen to allow dissipation of luminescence generated by exposure of a test component to UV radiation.

13. A test apparatus for monitoring the hygiene of a surface, the apparatus comprising a single service assay detection device container through which luminescence can be detected, wherein the container comprising a mixture of a plastic material and a light stabilizing UV blocking material for blocking at least a portion of the UV radiation to which the container may be exposed.

14. The test apparatus of claim 13 wherein the container comprises an olefin based plastic.

15. The test apparatus of claim 13 wherein the container comprises polypropylene.

16. The test apparatus of claim 13 wherein the container comprises a UV blocking material and a plastic, the UV blocking material characterized by the ability to at least partially block UV radiation, and wherein the material can be added to the plastic.

17. The test apparatus of claim 13 wherein the luminescence generated is detected by an instrument.

18. The test apparatus of claim 13 wherein the luminescence is generated by the reaction of luciferin and luciferase with ATP.

19. The test apparatus of claim 13 further comprising a luminometer, said luminometer configured to delay luminescence detection for a period of time, said period time chosen to allow luminescence from absorption of UV radiation, by a test component, to dissipate.

* * * * *

UNITED STATES PATENT AND TRADEMARK OFFICE
CERTIFICATE OF CORRECTION

| | | |
|---|---|---|
| PATENT NO. | : 8,663,975 B2 | Page 1 of 1 |
| APPLICATION NO. | : 13/477608 | |
| DATED | : March 4, 2014 | |
| INVENTOR(S) | : Charm et al. | |

It is certified that error appears in the above-identified patent and that said Letters Patent is hereby corrected as shown below:

On the title page item (56) under U.S. Patent Documents insert the following:

--US Patent No. 6043047 to Foote et al.
EP 1306435 to Kurosawa et al.--

In the Specification,

In Column 6, Line 54, finols should read "fmoles"

Signed and Sealed this
Twenty-fifth Day of August, 2015

Michelle K. Lee
*Director of the United States Patent and Trademark Office*